US012597501B2

(12) United States Patent
Yeh et al.

(10) Patent No.: US 12,597,501 B2
(45) Date of Patent: Apr. 7, 2026

(54) INTRADIALYTIC ANALYSIS METHOD AND ANALYSIS APPARATUS FOR DIALYSIS

(71) Applicant: Wistron Corporation, New Taipei City (TW)

(72) Inventors: Chih-Hsin Yeh, New Taipei City (TW); Chih-Yi Chien, New Taipei City (TW); Chih-Feng Kuo, New Taipei City (TW); Ting-Hui Lee, New Taipei City (TW)

(73) Assignee: Wistron Corporation, New Taipei City (TW)

( * ) Notice: Subject to any disclaimer, the term of this patent is extended or adjusted under 35 U.S.C. 154(b) by 1123 days.

(21) Appl. No.: 17/530,484

(22) Filed: Nov. 19, 2021

(65) Prior Publication Data

US 2023/0134865 A1     May 4, 2023

(30) Foreign Application Priority Data

Oct. 28, 2021     (TW) .................................. 110140157

(51) Int. Cl.
G16H 20/40 (2018.01)
A61M 1/16 (2006.01)
G16H 50/20 (2018.01)

(52) U.S. Cl.
CPC .......... G16H 20/40 (2018.01); A61M 1/1613 (2014.02); A61M 2205/52 (2013.01); G16H 50/20 (2018.01)

(58) Field of Classification Search
CPC .................................................... G16H 20/40
See application file for complete search history.

(56) References Cited

U.S. PATENT DOCUMENTS

| | | |
|---|---|---|
| 10,342,910 B2 | 7/2019 | Atallah et al. |
| 2011/0066006 A1 | 3/2011 | Banet et al. |
| 2015/0045713 A1 | 2/2015 | Attalah et al. |
| 2019/0217002 A1 | 7/2019 | Urakabe |
| 2020/0337647 A1 | 10/2020 | Chen |

(Continued)

FOREIGN PATENT DOCUMENTS

| | | |
|---|---|---|
| CN | 104346521 | 2/2015 |
| CN | 111939353 | 11/2020 |

(Continued)

OTHER PUBLICATIONS

Chen, Jin-Bor, et al. "Deep learning for intradialytic hypotension prediction in hemodialysis patients." IEEE Access 8 (2020): 82382-82390. (Year: 2020).*

(Continued)

*Primary Examiner* — Jesse P Frumkin
(74) *Attorney, Agent, or Firm* — JCIPRNET

(57) ABSTRACT

An intradialytic analysis method and an analysis apparatus for dialysis are provided. One or more input features are obtained. The input features include variance relation between current data and previous data of an operating parameter related to a dialysis machine and data related to a tester. Future data is predicted according to the input features through one or more prediction models. The future data includes blood pressure information and a predicted result of intradialytic hypotension at a future time point. Therefore, intradialytic hypotension can be predicted with high accuracy.

16 Claims, 4 Drawing Sheets

(56) References Cited

U.S. PATENT DOCUMENTS

| | | | |
|---|---|---|---|
| 2020/0397972 A1 | 12/2020 | Ku et al. | |
| 2021/0193317 A1* | 6/2021 | Kotanko | G16H 50/70 |
| 2022/0019892 A1* | 1/2022 | Ni | G06N 5/01 |
| 2022/0093261 A1* | 3/2022 | Noshay | G16H 50/30 |
| 2023/0040480 A1 | 2/2023 | Urakabe | |
| 2023/0094657 A1* | 3/2023 | Lee | G16H 20/40 705/2 |

FOREIGN PATENT DOCUMENTS

| | | |
|---|---|---|
| CN | 112957553 | 6/2021 |
| EP | 2835143 | 2/2015 |
| EP | 3511033 | 7/2019 |
| JP | 2018043003 | 3/2018 |
| JP | 2021108908 | 8/2021 |
| TW | I693062 | 5/2020 |
| TW | I710352 | 11/2020 |
| TW | 202100093 | 1/2021 |

OTHER PUBLICATIONS

Yang, Jiun-Yi, et al. "Differencing time series as an important feature extraction for intradialytic hypotension prediction using machine learning." 2021 IEEE 3rd Eurasia Conference on Biomedical Engineering, Healthcare and Sustainability (ECBIOS). IEEE, 2021. (Year: 2021).*

Men-Tai Wu et al., "Dialysis Hypotension," Journal of Internal Medicine of Taiwan, vol. 22, Oct. 2011, pp. 324-334.

Jennifer E. Flythe et al., "Association of Mortality Risk with Various Definitions of Intradialytic Hypotension," Journal of the American Society of Nephrology, vol. 26, May 2014, pp. 1-12.

University Hospitals Birmingham, "Standard Operating Procedures (SOPs) for the Management of a Patient's Haemodialysis Care," Sep. 2017, pp. 1-50.

"Office Action of Japan Counterpart Application", issued on Jul. 25, 2023, p. 1-p. 3.

"Office Action of Japan Counterpart Application", issued on Jan. 10, 2023, p. 1-p. 3.

"Search Report of Europe Counterpart Application", issued on May 25, 2022, p. 1-p. 9.

"Office Action of Taiwan Counterpart Application", issued on May 20, 2022, p. 1-p. 10.

* cited by examiner

| Resample and retrain | ⟋ S510 |

| Predict future data according to a new prediction model | ⟋ S530 |

INTRADIALYTIC ANALYSIS METHOD AND ANALYSIS APPARATUS FOR DIALYSIS

CROSS-REFERENCE TO RELATED APPLICATION

This application claims the priority benefit of Taiwan application serial no. 110140157, filed on Oct. 28, 2021. The entirety of the above-mentioned patent application is hereby incorporated by reference herein and made a part of this specification.

BACKGROUND

Technical Field

The disclosure relates to a detection technique, and particularly relates to an intradialytic analysis method and an analysis apparatus for dialysis.

Description of Related Art

Intradialytic hypotension is the most common complication of dialysis patients, which not only affects the quality of life of patients, but may also easily cause arrhythmia and chronic or acute cardiovascular and cerebrovascular ischemia. When intradialytic hypotension occurs, medical staff must immediately interrupt the dialysis treatment of a patient and perform clinical treatment to avoid continuous lowering of blood pressure. Repeated occurrence of intradialytic hypotension will lead to insufficient urinary toxin clearance rate and dehydration, and may even worsen the original symptoms of uremia and heart failure in the long term, thereby increasing the mortality rate of dialysis patients.

At present, there is still a lack of consensus on the definition of intradialytic hypotension worldwide, which also examines the clinical accuracy of the development of hypotension early warning systems. For the medical staff, it is necessary to maintain a high degree of concentration during the dialysis treatment. In addition to immediate treatment of dehydration speed and dialysis temperature of the patient, sudden changes in blood pressure still require the accumulation of personal experience of the medical staff to respond in time. However, there is no established standard for parameter adjustment currently, so there is a possibility of misjudgment. It can be seen that there are still shortcomings in existing intradialytic hypotension early warning mechanisms.

SUMMARY

The disclosure provides an intradialytic analysis method and an analysis apparatus for dialysis, which can warn of intradialytic hypotension in advance.

The intradialytic analysis method of an embodiment of the disclosure includes (but is not limited to) the following steps. One or more input features are obtained. The input features include variance relation between current data and previous data of an operating parameter related to a dialysis machine and data related to a tester. Future data is predicted according to the input features through one or more prediction models. The future data includes blood pressure information and a predicted result of intradialytic hypotension at a future time point.

The analysis apparatus for dialysis of an embodiment of the disclosure includes (but is not limited to) a storage and a processor. The storage is configured to store a code. The processor is coupled to the storage. The processor is configured to load and execute the code to execute the following steps. One or more input features are obtained. The input features include variance relation between current data and previous data of an operating parameter related to a dialysis machine and data related to a tester. Future data is predicted according to the input features through one or more prediction models. The future data includes blood pressure information and a predicted result of intradialytic hypotension at a future time point.

Based on the above, the intradialytic analysis method and the analysis apparatus for dialysis of the embodiments of the disclosure further consider a new variable (for example, the variance relation between the current data and the previous data) that affects intradialytic hypotension to improve the accuracy of prediction. In this way, intradialytic hypotension that is about to occur for a patient can be predicted in advance, and nursing staff can be further notified to make the appropriate treatment to reduce the occurrence of interruption of dialysis, thereby reducing the mortality rate of patients and improving the quality of medical care.

In order for the features and advantages of the disclosure to be more comprehensible, the following specific embodiments are described in detail in conjunction with the accompanying drawings.

DETAILED DESCRIPTION OF DISCLOSED EMBODIMENTS

Figure 1:
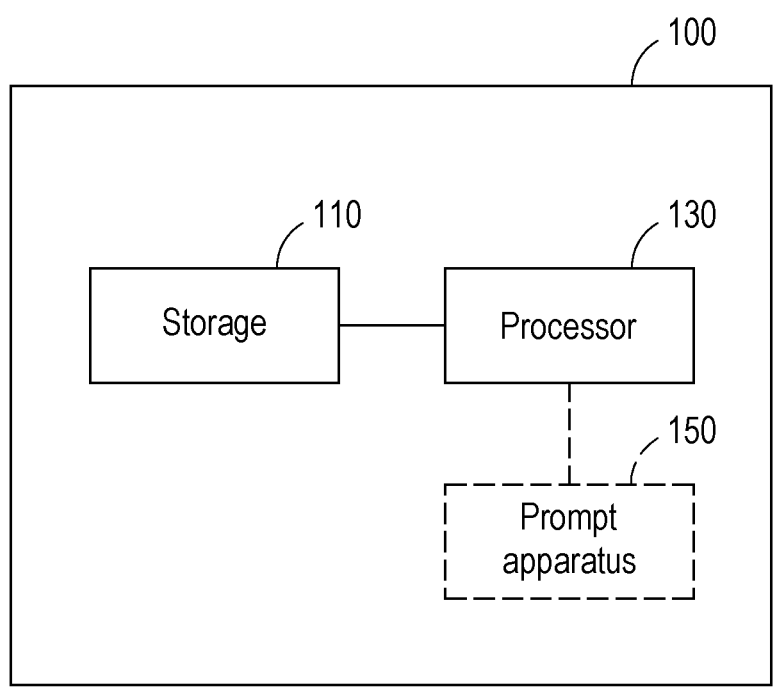
FIG. 1 is a block diagram of elements of an analysis apparatus according to an embodiment of the disclosure.

FIG. 1 is a block diagram of elements of an analysis apparatus 100 according to an embodiment of the disclosure. Please refer to FIG. 1, the analysis apparatus 100 includes (but is not limited to) a storage 110 and a processor 130. The analysis apparatus 100 may be a hemodialysis machine, a control instrument, or any electronic apparatus (for example, a smart phone, a tablet computer, a server, a cloud host, or a computer host) capable of computing physiological data of a user.

The storage 110 may be any type of fixed or removable random access memory (RAM), read only memory (ROM), flash memory, hard disk drive (HDD), solid-state drive (SSD), or similar elements. In an embodiment, the storage 110 is configured to record codes, software modules, configuration layouts, data (for example, physiological parameters, biochemical test parameters, basic data, operating parameters, features, data collection at each time point, predicted results, etc.), or files, and the embodiment thereof will be detailed later.

The processor 130 is coupled to the storage 110. The processor 130 may be a central processing unit (CPU), a graphic processing unit (GPU), other programmable general-purpose or specific-purpose microprocessors, digital signal processors (DSPs), programmable controllers, field programmable gate arrays (FPGAs), application-specific integrated circuits (ASICs), neural network accelerators, other similar elements, or a combination of the above elements. In an embodiment, the processor 130 is configured to execute all or part of the operations of the analysis apparatus 100, and may load and execute various codes, software modules, files, and data recorded by the storage 110. In some embodiments, the functions of the processor 130 may be implemented through software or a chip.

In an embodiment, the analysis apparatus 100 further includes a prompt apparatus 150. The prompt apparatus 150 may be a display, a light emitting diode (LED), a speaker, a buzzer, a communication transceiver, other apparatuses that can provide visual or auditory effects, or a combination thereof. In some embodiments, the prompt apparatus 150 is configured to alert, for example, to display an alarm notification, flash light, emit an alert sound, or send an alert message. However, the alert manner may still be changed according to actual requirements and is not limited in the embodiment of the disclosure.

Hereinafter, the method according to the embodiment of the disclosure will be described in conjunction with various elements and modules in the analysis apparatus 100. Each process of the method may be adjusted according to the implementation situation and is not limited thereto.

Figure 2:
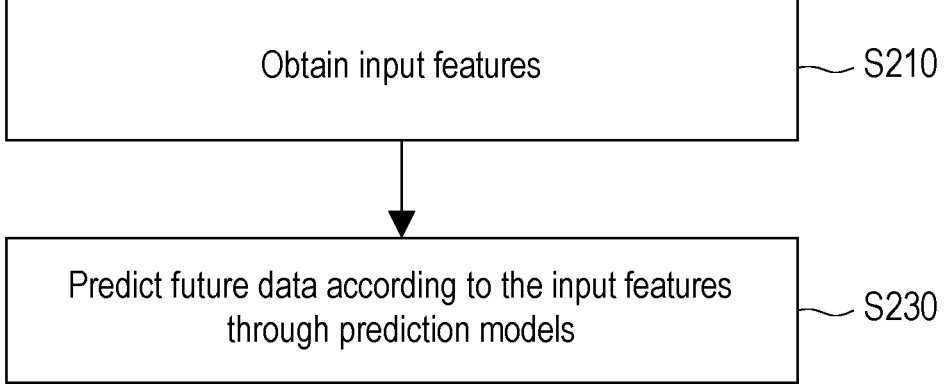
FIG. 2 is a flowchart of an intradialytic analysis method according to an embodiment of the disclosure.

FIG. 2 is a flowchart of an intradialytic analysis method according to an embodiment of the disclosure. Please refer to FIG. 2. The processor 130 obtains one or more input features (Step S210). Specifically, the input features are input data for subsequent evaluation of blood pressure information and/or intradialytic hypotension. The processor 130 may obtain the input features or corresponding raw data via an input/output apparatus, the storage 110, an external storage apparatus, or a network.

In an embodiment, the input features include variance relation between measured current data and previous data of an operating parameter related to a (hemo)dialysis machine and/or data related to a tester (for example, a patient undergoing dialysis treatment or other users).

For example, Table (1) is an example illustrating the operating parameter of the dialysis machine:

TABLE 1

| Original field name | Field description | Field name | Data definition |
|---|---|---|---|
| TARGET_UF | Target dehydration | target_uf | Numeric |
| TOTAL_UF | Total dehydration | total_uf | Numeric |
| UF | Dehydration rate | uf | Numeric |
| BLOOD_FLOW | Blood flow rate | blood_flow | Numeric |
| TEMP | Dialysate temperature | dia_temp_value | Numeric |
| CONDUCTIVITY | Dialysate conductivity | conductivity | Numeric |
| VENOUS | Venous pressure | venous | Numeric |
| TIME | Dialysis time (minutes) | time | Numeric |
| DIA_FLOW | Dialysate flow | dia_flow | Numeric |

For another example, Table (2) (related to physiological parameters) and Table (3) (related to biochemical test results) are examples of related parameters of the tester:

TABLE 2

| Original field name | Field description | Field name | Data definition |
|---|---|---|---|
| MAX_BLOOD | Systolic blood pressure | sbp | Numeric |
| MIN_BLOOD | Diastolic blood pressure | dbp | Numeric |
| PULSE | Pulse | pulse | Numeric |
| HD_BT | Body temperature | temperature | Numeric |
| BW_STAND | Dry weight | dryweight | Numeric |
| BEGIN_WEIGHT | Weight before dialysis | begin_weight | Numeric |
| END_WEIGHT | Weight after dialysis | end_weight | Numeric |
| LAST_END_WEIGHT | End-of-dialysis weight of patient | last_end_weight | Numeric |

TABLE 3

| Original field name | Variable description | Field name | Data definition |
|---|---|---|---|
| Hb | Heme | hb | Numeric |
| Hct | Hematocrit | hct | Numeric |
| Albumin | Albumin | albumin | Numeric |
| P | Phosphorus | p | Numeric |
| K | Potassium | k | Numeric |

The current data refers to the operating parameters, the physiological parameters, the biochemical test parameters, and/or other monitoring parameters measured at a current time point. It should be noted that the current time point of measurement may be different from a time point of processing the parameters. In some embodiments, the closest measurement time point may be used as the current time point, but not limited thereto.

On the other hand, the previous data refers to the operating parameters, the physiological parameters, the biochemical test parameters, and/or other monitoring parameters measured at one or more time points before the current time point. That is, a previous time point is earlier than the current time point. For example, if the current time point is 12 o'clock, then the previous time point may be 11 o'clock or 11:30. It should be noted that depending on the requirements of the user, an interval between two adjacent time points may be fixed or may vary.

In an embodiment, according to clinical experience, the variance relation between the previous data and the current data affects blood pressure changes. The variance relation may be a numerical difference between two adjacent time points. For example, the variance relation includes an ultrafiltration rate change, a conductivity change, a dialysate temperature change, and/or a blood flow change between two adjacent time points.

Figure 3:
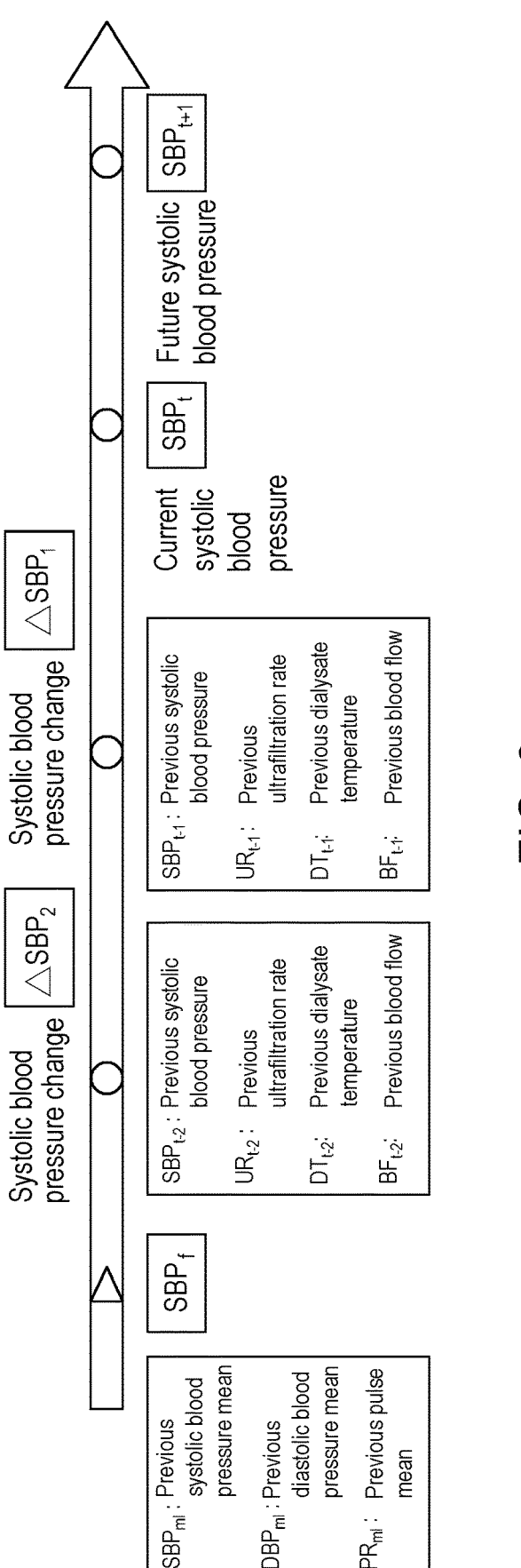
FIG. 3 is a schematic diagram of training data analysis for establishing a prediction model according to an embodiment of the disclosure.

The variance relation may be changes in data between t and t−1 or between t−1 and t−2, where t is the current time point, and t−1 and t−2 are the previous time points. For example, FIG. 3 is a schematic diagram of training data analysis for establishing a prediction model according to an embodiment of the disclosure. Please refer to FIG. 3. It is assumed that the current time point is t, the previous time points are t−1 and t−2, and a future time point is t+1. The processor 130 may obtain or calculate a systolic blood pressure change $\Delta SBP_1$ (for example, a current systolic blood pressure $SBP_t$—a previous systolic blood pressure $SBP_{t-1}$) between the current time point t and the previous time point t−1 and/or a systolic blood pressure change $\Delta SBP_2$ (for example, the previous systolic blood pressure $SBP_{t-1}$—a previous systolic blood pressure $SBP_{t-2}$) between the previous time points t−1 and t−2. Similarly, the processor 130 may use a difference between previous ultrafiltration rates $UR_{t-1}$ and $UR_{t-2}$ as the ultrafiltration rate change, a difference between previous dialysate temperatures $DT_{t-1}$ and $DT_{t-2}$ as the dialysate temperature change, and/or a difference between previous blood flows $BF_{t-1}$ and $BF_{t-2}$ as the blood flow change.

In another embodiment, the variance relation may be a dehydration rate difference, a venous pressure difference, a dialysis time difference, a dialysate flow difference, a systolic blood pressure difference, and/or a pulse difference between the current time point t and the previous time point t−1, between the previous time point t−1 and the previous time point t−2, or between two other adjacent time points.

In addition to the features of the variance relation, in an embodiment, the monitoring parameters further include the previous data. The previous data includes blood pressure information before a current dialysis operation and/or statistical information of a previous dialysis operation. Taking FIG. 3 as an example, the blood pressure information before the current dialysis operation is a first previous systolic blood pressure $SBP_f$ measured before the start of the dialysis operation. The statistical information of the previous dialysis operation is a previous systolic blood pressure mean $SBP_{m1}$, a previous diastolic blood pressure mean $DBP_{m1}$, and a previous pulse mean $RP_{m1}$ of the previous or more previous dialysis operations. It should be noted that the statistical information may also be a median, a mode, or other statistical indicators and is not limited in the embodiment of the disclosure. In addition, the previous data may further include parameters such as a previous blood pressure and a previous dialysate temperature of the current dialysis operation.

In an embodiment, the input features include the basic data of the tester. For example, Table (4) is an example illustrating the basic data:

TABLE 4-continued

| Original field name | Original field description | Field name | Data definition |
|---|---|---|---|
| HEM_FIRST_DT | First day of dialysis | | |
| DISEASE_1 | Medical History-Diabetes (Y = Yes) | DM | (1 = Yes, 0 = None) |
| DISEASE_2 | Medical History-Hypertension (Y = Yes) | HT | (1 = Yes, 0 = None) |
| DISEASE_3 | Medical history-Cardiac disease (Y = Yes) | CAD | (1 = Yes, 0 = None) |

It should be noted that the basic data may further include medication records and/or disease history.

In an embodiment, the input features include external data. For example, environmental parameters such as climate, temperature, and humidity.

In an embodiment, the processor 130 converts the operating parameter of the dialysis machine, the measured data (for example, the physiological parameters, the biochemical test parameters, or the basic data) related to the tester, and/or the external data into the input features. That is, variable conversion. The input features conform to an input format of a prediction model for subsequent evaluation. In an embodiment, the processor 130 may perform field definition/description, number ratio processing, judge missing values, convert categorical data into a uniform numerical format (for example, a binary, decimal, or hexadecimal format), calculate the variance relation, and other conversions on the above parameters or data to generate the input features. For example, Table (5), Table (6), and Table (7) are examples illustrating the converted input features:

TABLE 4

| Original field name | Original field description | Field name | Data definition |
|---|---|---|---|
| BIRTH_DATE | Date of birth | | |
| SEX | Gender (M = Male, F = Female) | gender | (1 = Male, 0 = Female) |

TABLE 5

| Conversion field name | Field description | Data conversion definition |
|---|---|---|
| age | Age | (Today-BIRTH_DATE)/365.25 |
| dialysis year | Dialysis year | (Today-HEM_FIRST_DT)/365.25 |

TABLE 6

| Conversion field name | Field description | Data conversion definition |
|---|---|---|
| total_ufb | Previous total dehydration | $total\_uf_{t-1}$ |
| ufb | Previous dehydration rate | $uf_{t-1}$ |
| blood_flowb | Previous blood flow rate | $blood\_flow_{t-1}$ |
| tempb | Previous dialysate temperature | $temp_{t-1}$ |
| conductivityb | Previous dialysate conductivity | $conductivity_{t-1}$ |
| venousb | Previous venous pressure | $venous_{t-1}$ |
| timeb | Previous dialysis time (minutes) | $time_{t-1}$ |
| dia_flowb | Previous dialysate flow | $dia\_flow_{t-1}$ |
| Δ uf | Difference between two previous dehydration rates | $uf_t - uf_{t-1}$ |
| Δ blood_flow | Difference between two previous blood flow rates | $blood\_flow_t - blood\_flow_{t-1}$ |
| Δ dia_temp_value | Difference between two previous the dialysate temperatures | $temp_t - temp_{t-1}$ |
| Δ conductivity | Difference between two previous dialysate conductivities | $conductivity_t - conductivity_{t-1}$ |

TABLE 6-continued

| Conversion field name | Field description | Data conversion definition |
|---|---|---|
| Δ venous | Difference between two previous venous pressures | $venous_t\text{-}venous_{t-1}$ |
| Δ time | Difference between two previous dialysis times (minutes) | $time_t\text{-}time_{t-1}$ |
| Δ dia_flow | Difference between two previous dialysate flows | $dia\_flow_t\text{-}dia\_flow_{t-1}$ |
| ufmean | Mean dehydration rate of previous dialysis | — |
| tempmean | Mean dialysate temperature of previous dialysis | — |
| conductivitymean | Mean dialysate conductivity of previous dialysis | — |
| venousmean | Mean venous pressure of previous dialysis | — |
| dia_flowmean | Mean dialysate flow rate of previous dialysis | — |
| ufweight | Target dehydration divided by dry weight | target_uf/dryweight |

TABLE 7

| Field name | Variable description | Data definition |
|---|---|---|
| first_sbp | Systolic blood pressure at start of dialysis | — |
| sbpb | Previous systolic blood pressure | $sbp_{t-1}$ |
| dbpb | Previous diastolic blood pressure | $dbp_{t-1}$ |
| pulseb | Previous pulse | $pulse_{t-1}$ |
| Δ sbp | Difference between two previous systolic blood pressures | $sbp_t\text{-}sbp_{t-1}$ |
| Δ dbp | Difference between two previous diastolic blood pressures | $dbpt\text{-}dbp\ t\text{-}1$ |
| Δ pulse | Difference between two previous pulses | $pulset\text{-}pulse\ t\text{-}1$ |
| sbpmeanlast | Mean systolic blood pressure of previous dialysis | — |
| dbpmeanlast | Mean diastolic blood pressure of previous dialysis | — |
| pulsemeanlast | Mean pulse of previous dialysis | — |
| weight_prop | Weight difference before and after dialysis as a ratio of start-of-dialysis weight | (begin_weight-last_end_weight)/ (begin_weight) |

In an embodiment, during training of the prediction model, the processor 130 may perform outlier processing on the above parameters or data to exclude outliers in an unreasonable range. For example, Table (8) is an example illustrating exclusion ranges corresponding to the parameters:

TABLE 8

| Field name | Exclusion range |
|---|---|
| time | >300 |
| sbp | <30, >300 |
| dbp | <30, >300 |
| temperature | <32, >40 |
| temp(° C.) | <32, >40 |
| conductivity | <10, >20 |
| uf | <0, >3 |
| target_uf | <0, >10 |
| dryweight | <30, >200 |
| blood_flow | <0, >700 |
| pulse | <30, >200 |

For example, the processor 130 deletes data with a pulse of 20.

Please refer to FIG. 2. The processor 130 predicts future data according to the input features through one or more prediction models (Step S230). Specifically, the future data includes blood pressure information and a predicted result of intradialytic hypotension at a future time point. Taking FIG. 3 as an example, the future time point t+1 is 12:30, and the current time point t is 12 o'clock. In an embodiment, the blood pressure information at the future time point is a future systolic blood pressure (a future systolic blood pressure $SBP_{t+1}$ as shown in FIG. 3). In some embodiments, the processor 13 may determine and/or compare a hypotension threshold value based on the blood pressure information for the evaluation of intradialytic hypotension. In an embodiment, the predicted result of intradialytic hypotension is an occurrence probability of intradialytic hypotension. In another embodiment, the predicted result of intradialytic hypotension is the result of occurrence of intradialytic hypotension or no occurrence of intradialytic hypotension.

It is worth noting that Document 1 "Dialysis Hypotension" (Authors: Men-Tai Wu, Chih-Chao Yang, King-Kwan Lam, and Chien-Te Lee) published by College of Medicine, Chang Gung University in 2011 shows that intradialytic hypotension is related to parameters such as systolic function, diastolic function, blood volume changes, pulse output, and dialysate temperature. In 2015, Document 2 "Association of Mortality Risk with Various Definitions of Intradialytic Hypotension" published in Journal of Clinical Epidemiology further defines Fall20Nadir90 as a hypotension threshold value with (systolic blood pressure before dialysis–lowest intradialytic blood pressure)≥20 mm-Hg and lowest intradialytic blood pressure<90 mm-Hg.

In an embodiment, the hypotension threshold value for evaluating intradialytic hypotension may be based on Document 2. For example, the systolic blood pressure before dialysis of the patient is 120 mm-Hg. Therefore, during dialysis, if the systolic blood pressure meets the Fall20Nadir90 condition (that is, the systolic blood pressure is lower than 90 mm-Hg and is different from the systolic blood pressure before dialysis by 20 mm-Hg), the same may be recorded as an intradialytic blood pressure drop (hypotension) event. However, during dialysis, if the measured systolic blood pressure is greater than 90 mm-Hg, the same is a normal event without blood pressure drop (that is, without intradialytic hypotension). In other embodiments, the definition of intradialytic hypotension may still be changed according to actual requirements and is not limited by the disclosure.

In an embodiment, the prediction model is established through one or more machine learning algorithms. The machine learning algorithm may be regression analysis algorithm, eXtreme gradient boosting (XGboost) algorithm, light gradient boosting machine (LightGBM), bootstrap aggregating (Bagged) algorithm, neural network algorithm, least absolute shrinkage and selection operator (LASSO) algorithm, random forest algorithm, support vector regression algorithm, or other algorithms. The machine learning algorithm may analyze training data/samples to obtain rules therefrom, so as to predict unknown data through the rules. The prediction model is a machine learning model constructed after learning and inferences data to be evaluated accordingly.

It should be noted that the training data of the prediction model is the same as or related to the parameters or data types corresponding to the input features. For example, the operating parameter of the dialysis machine, a physiological state of the tester, the basic data, and/or the external data. In some embodiments, the training data further includes actual data (that is, future blood pressure information and/or whether intradialytic hypotension actually occurs). Document 3 "Standard operation procedures (SOPs) for the management of a patient's haemodialysis care" provided by the University Hospitals Birmingham in 2017 illustrates the correlation between the input features of the embodiment of the disclosure and the predicted future data.

Figure 4:
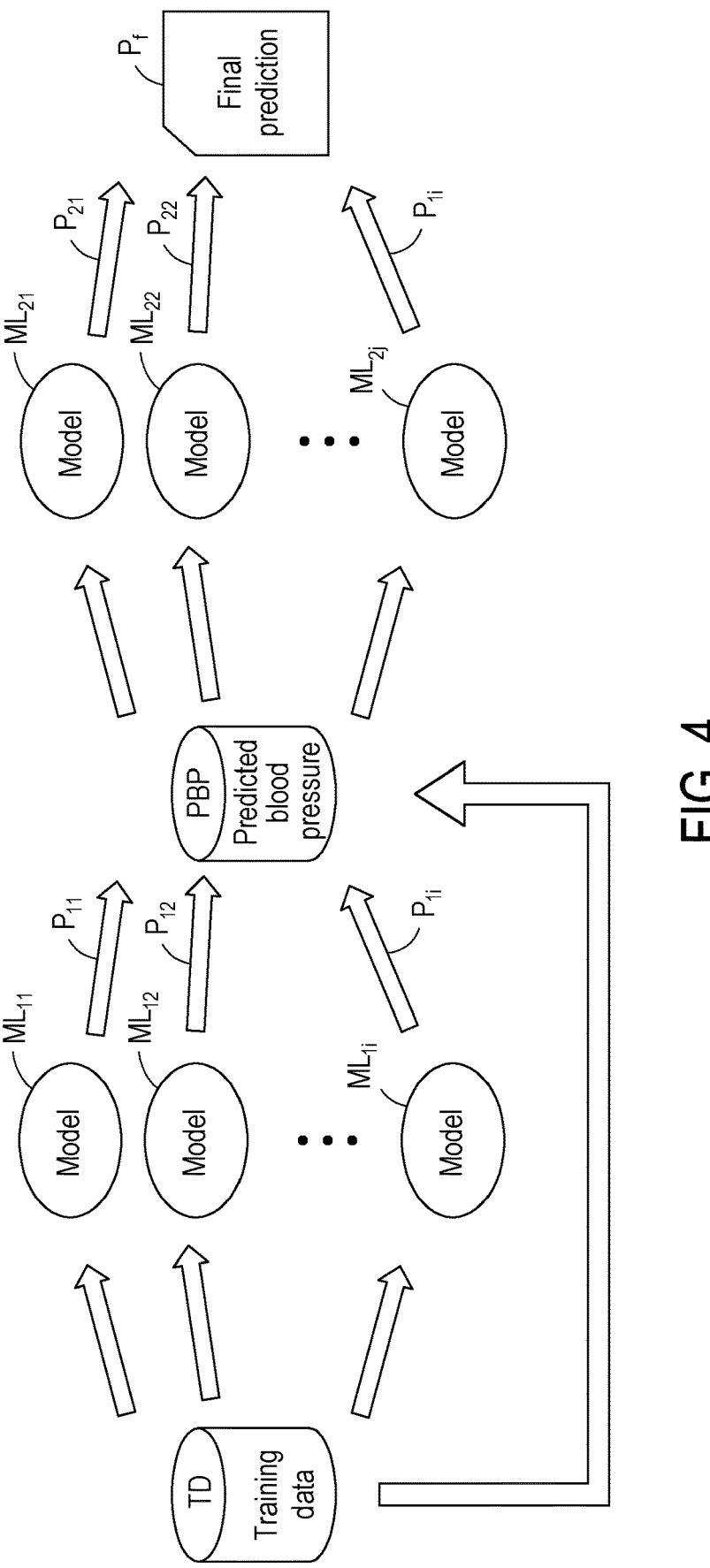
FIG. 4 is a schematic diagram of determining final future data according to an embodiment of the disclosure.

In an embodiment, the processor 130 determines final future data according to the future data predicted by multiple prediction models. The machine learning algorithms used by the prediction models may be the same or different, and the final future data also includes the blood pressure information and the predicted result of intradialytic hypotension at the future time point. For example, FIG. 4 is a schematic diagram of determining final future data according to an embodiment of the disclosure. Please refer to FIG. 4. It is assumed that the prediction model includes a first classification model and there are i first classification models $ML_{11}$ to $ML_{1i}$(where i is a positive integer greater than one). The first classification models $ML_{11}$ to $ML_{1i}$ sample the same, related, or similar training data TD but after training based on different machine learning algorithms (for example, regression analysis, XGBoost, neural network system, random forest, LASSO, support vector regression, neural network, etc.), the processor 130 uses the first classification models $ML_{11}$ to $ML_{1i}$ to respectively predict future data $P_{11}$ to $P_{1i}$, and determines the blood pressure information in final future data $P_f$ based on the future data $P_{11}$ to $P_{1i}$. For example, a statistical result (for example, arithmetic mean, weighted mean, or median) of a predicted blood pressure PBP (that is, the blood pressure information predicted by the first classification models $ML_{11}$ to $ML_{1i}$) of the future data $P_{11}$ to $P_{1i}$ is determined. The predicted blood pressure PBP may be used as one of the final future data.

In an embodiment, the processor 130 determines a statistical indicator of the future data predicted by the prediction models based on ensemble learning, and the statistical indicator is used as the final future data. The machine learning algorithms used by the prediction models are different. For example, the processor 130 sums up and averages the future data (for example, blood pressure values) obtained by using the prediction models respectively based on multivariate linear regression, LASSO, random forest, support vector regression, and neural network to be used as the final future data. More specifically, the processor 130 averages (or votes) through the concept of bagging to obtain a more stable (for example, lower variance) mean performance, and combines different prediction models through the concept of stacking for prediction. The literal meaning of bagging is to divide data into multiple bags, and then combine results of the bags. In terms of algorithm, after the training data is repeatedly sampled (and put back after being sampled) to generate multiple subsets, multiple models are sequentially established, and finally results of all the models are consolidated. If a regression problem is to be predicted, then all the results may be averaged; if a classification problem is to be predicted, then voting may be adopted to judge the classification that appears the most times. Compared with individual prediction models, the combination of several models can improve the accuracy of prediction. Taking FIG. 4 as an example, the processor 130 uses ensemble learning to determine the statistical indicator of the predicted blood pressure PBP of the future data $P_{11}$ to $P_{1i}$ predicted by the first classification models $ML_{11}$ to $ML_{1i}$.

In an embodiment, in addition to the one or more first classification models for predicting the blood pressure information in the future data, the embodiment of the disclosure further provides one or more second classification models for predicting the predicted result of intradialytic hypotension. It is worth noting that if the blood pressure information predicted by the first classification model is directly used to evaluate intradialytic hypotension using the Fall20Nadir90 condition, then there may be too many false alerts in a confidence interval. Therefore, in addition to the operating parameter of the dialysis machine, the physiological state of the tester, the basic data, and/or the external data, the predicted blood pressure information needs to be additionally considered. The processor 130 may determine the blood pressure information in the future data predicted by the first classification models, add the blood pressure information at the future time point predicted by the first classification models to the input features of the second classification models (that is, use the blood pressure information predicted by the first classification models as one of the input features of the second classification models), and determine the predicted result of intradialytic hypotension (that is, predict whether intradialytic hypotension will occur at the future time point) in the future data predicted by the second classification models according to the newly added input features of the blood pressure information at the future time point. In other words, the input features of the second classification model also include the blood pressure information at the future time point predicted by the first classification models in addition to the operating parameter of the dialysis machine, the physiological state of the tester, the basic data, and/or the external data. In addition, after considering the predicted blood pressure information, the processor 130 may use the Fall20Nadir90 condition or other definitions to evaluate intradialytic hypotension. In an embodiment, when training the second classification models, labelling may be first performed based on the operating parameter of the dialysis machine of each sample, the physiological state of the tester, the basic data, the external data, and the blood pressure information. After labeling whether an intradialytic hypotension event occurs, as training samples for training the second classification models, during labeling, the Fall20Nadir90 condition or other definitions of intradialytic hypotension may be used to judge whether intradialytic hypotension occurs in each sample to perform labelling, wherein the blood pressure information for training contains actual blood pressure information and may also contain predicted blood pressure information.

Taking FIG. 4 as an example, the processor 130 determines the predicted blood pressure PBP in the future data $P_{11}$ to $P_{1i}$ predicted by the first classification models $ML_{11}$ to $ML_{1i}$ based on ensemble learning. The processor 130 uses the statistical indicator of the predicted blood pressure PBP obtained based on the first classification models $ML_{11}$ to $ML_{1i}$ as one of the input features of second classification models $ML_{21}$ to $ML_{2j}$ (where j is a positive integer greater than one). The j second classification models $ML_{21}$ to $ML_{2j}$ may be established based on different machine learning algorithms (for example, regression analysis, XGBoost, neural network system, random forest, LASSO, support vector regression, neural network, etc.). Then, the processor 130 again determines the predicted result of intradialytic hypotension in the future data predicted by the second classification models $ML_{21}$ to $ML_{2j}$ according to the input features including the predicted blood pressure PBP and based on ensemble learning. For example, a majority vote of ensemble learning is used to judge whether intradialytic hypotension occurs. As such, a final prediction $P_f$ may be obtained. In an embodiment, the predicted result of intradialytic hypotension output by each second classification model is 0 or 1, wherein 0 represents that no intradialytic hypotension occurs and 1 represents that intradialytic hypotension occurs, and the majority vote of ensemble learning is used to judge the predicted result of each second classification model. For example, if the number of output 1 of the second classification models is greater than the number of output 0, the processor 130 will judge that intradialytic hypotension occurs. In another embodiment, the processor 130 may integrate the predicted blood pressure PBP into the final predicted $P_f$ as the future data.

It should be noted that in other embodiments, the first classification models may also predict both the blood pressure information and the predicted result of intradialytic hypotension at the future time point.

Each prediction model may also be retrained regularly or based on a specific event to adjust the parameters accordingly. In addition, medical data may have the issue of unbalanced classification. For example, Table (9) is an example illustrating the relationship of number of events between the predicted result of intradialytic hypotension and the actual data:

TABLE 9

| Predicted result | Actual data | |
| --- | --- | --- |
| | No intradialytic hypotension actually occurs | Intradialytic hypotension actually occurs |
| Predicted no intradialytic hypotension | 14821 | 8770 |
| Predicted intradialytic hypotension | 605 | 1626 |

In Table (9), the number of events of no intradialytic hypotension actually occurring (for example, 14821+605=15426) is significantly more than the number of events of intradialytic hypotension actually occurring (for example, 870+1626=2496), so the same belongs to "unbalanced data".

Figure 5:
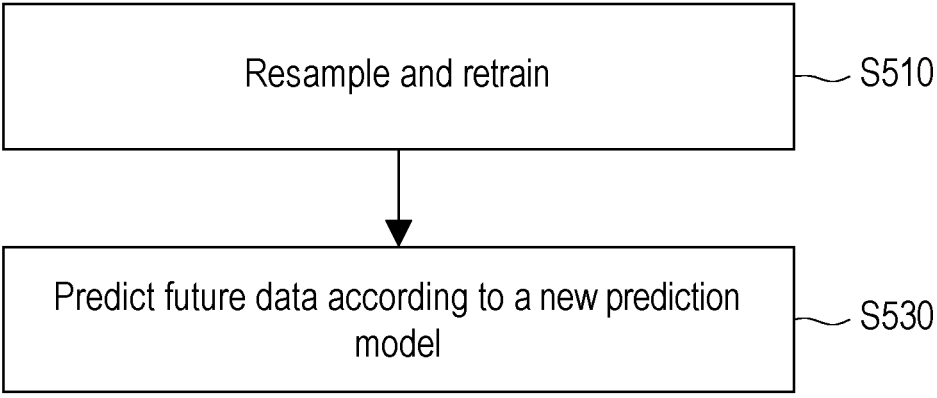
FIG. 5 is a flowchart of resampling according to an embodiment of the disclosure.

In order to correct the "unbalanced data" and improve the accuracy and sensitivity of prediction, the embodiment of the disclosure may further resample the training data. FIG. 5 is a flowchart of resampling according to an embodiment of the disclosure. Please refer to FIG. 5. The processor 130 resamples the training data used by the prediction model (for example, the second classification model) for predicting intradialytic hypotension according to the future data and the corresponding actual data, and establishes a new prediction model according to the resampled training data (Step S510).

For example, the processor 130 judges whether the number of different predicted results in the actual data is unbalanced (for example, a number difference or a number ratio is higher than a corresponding threshold value). In addition, resampling may be copying and/or deleting a corresponding training sample/data of a specific predicted result.

In an embodiment, the processor 130 may adjust the number of one or more positive samples and one or more negative samples in the training data according to the number ratio. The number ratio is an expected ratio of the number of positive samples to the number of negative samples. For example, 1:1, 7:8, or 10:12. The positive sample is a sample related to intradialytic hypotension occurring in the actual data (that is, intradialytic hypotension actually occurs), and the negative sample is a sample related to no intradialytic hypotension occurring in the actual data (that is, no intradialytic hypotension actually occurs). In other words, the positive samples are the samples (for example, the operating parameter of the dialysis machine, parameters related to the physiological state of the tester, the basic data, etc.) in which intradialytic hypotension is known to actually occur in the training data. The negative samples are the samples (for example, the operating parameter of the dialysis machine, the parameters related to the physiological state of the tester, the basic data, etc.) in which no intradialytic hypotension is known to actually occur in the training data. The processor 130 may resample the training data, so that the ratio of the resampled positive samples to negative samples is the same as or close to the set number ratio.

In an embodiment, the processor 130 may copy the positive sample and/or the negative sample, and/or delete the positive sample and/or the negative sample, so that the ratio of the resampled positive samples to negative samples is the same as or close to the set number ratio. Copying data causes more than two samples in the training data to be the same while deleting data causes the amount of training data to be reduced.

Taking Table (9) as an example, it is assumed that the expected number ratio is 1:1. For an oversampling method, the processor 130 may randomly copy at least one of the positive samples. For an undersampling method, the processor 130 may randomly delete at least one of the negative samples. For a combined method of oversampling and undersampling, the processor 130 may randomly copy the positive samples and randomly delete the negative samples according to a number ratio of 0.5.

The processor 130 may retrain the resampled training data by itself or provide the resampled training data to an external cloud host for retraining and build a new prediction model. Then, the processor 130 may input the input features corresponding to the current time point (the time point after prediction through the prediction model) into the new prediction model, and then predict future data again through the new prediction model (Step S530). For example, the processor 130 inputs the input feature corresponding to 11:30 to the prediction model to predict the future data at 12 o'clock. When the actual data at 12 o'clock is known (that is, whether intradialytic hypotension actually occurs), the processor 130 uses the actual data obtained at 12 o'clock and the operating parameters, physiologically related parameters, and the external data as the training data and resamples, for example, through the oversampling method, the undersampling method, or the combined method of oversampling and undersampling to establish the new prediction model. Next, the processor 130 uses the new prediction model to judge the future data corresponding to the input feature at 12 o'clock (for example, to predict the future data at 12:30).

In some embodiments, the processor 130 may further adopt sensitivity, false omission rate (FOR), specificity, and/or false positive rate (FPR) to evaluate the result of the prediction model. The sensitivity is cases where the prediction model predicts that intradialytic hypotension occurs as a ratio of all cases where intradialytic hypotension actually occurs. Therefore, the higher the sensitivity, the better the result. The false omission rate is cases where intradialytic hypotension actually occurs as a ratio of all cases where no intradialytic hypotension is predicted. Therefore, the lower the false omission rate, the better the result. The specificity is cases where the prediction model predicts that no intradialytic hypotension occurs as a ratio of all cases where no intradialytic hypotension actually occurs. Therefore, the higher the specificity, the better the result. In addition, the false positive rate is cases where intradialytic hypotension is predicted as a ratio of all cases where no intradialytic hypotension actually occurs. Therefore, the lower the false positive rate, the better the result. Experiments have proved that compared with the prediction model, the resampled new prediction model can effectively improve the indicator values.

In addition to predicting the future data, in an embodiment, the processor 130 may emit a warning notification according to the predicted result of intradialytic hypotension through the prompt apparatus 150. For example, if the predicted result is that an intradialytic hypotension event occurs or an occurrence probability exceeds a corresponding threshold value, then the processor 130 may display a warning text, emit an alert sound, or send a message to a nurse counter. For another example, if the predicted result is no intradialytic hypotension occurs or the occurrence probability does not exceed the corresponding threshold value, there is no need to issue the warning notification.

In summary, in the intradialytic analysis method and the analysis apparatus for dialysis of the embodiments of the disclosure, more new variables (for example, the variance relation, the previous data, etc.) that affect changes in intradialytic blood pressure are considered to directly estimate the blood pressure information and whether intradialytic hypotension occurs at the future time point in conjunction with the prediction model. In order to conform to the format of the prediction model, the original data or the parameters may be further calculated and/or converted to become the input features that conform to the model. The model is corrected through resampling to improve the accuracy, the sensitivity, and the specificity of prediction. In addition, in order to meet the requirements of practical applications, the definition of intradialytic hypotension may be adjusted.

Although the disclosure has been disclosed in the above embodiments, the embodiments are not intended to limit the disclosure. Persons skilled in the art may make some changes and modifications without departing from the spirit and scope of the disclosure. The protection scope of the disclosure shall be defined by the appended claims.

What is claimed is:

1. An intradialytic analysis method, comprising:
obtaining at least one input feature, wherein the at least one input feature comprises variance relation between current data and previous data of an operating parameter related to a dialysis machine and data related to a tester;
predicting future data according to the at least one input feature through at least one prediction model, wherein the future data comprises blood pressure information and a predicted result of intradialytic hypotension at a future time point, the at least one prediction model comprises a plurality of first classification models and a plurality of second classification models, and the step of predicting the future data according to the at least one input feature through the at least one prediction model comprises:
determining final future data according to the future data predicted by the first and second prediction models, wherein the final future data comprises the blood pressure information and the predicted result of the intradialytic hypotension at the future time point, the blood pressure information indicates systolic blood pressure, and the step of determining the final future data according to the future data predicted by the prediction models comprises:
determining the blood pressure information in the future data predicted by the first classification models; and
determining the predicted result of the intradialytic hypotension in the future data predicted by the second classification models according to the at least one input feature and the blood pressure information,
resampling a plurality of training data used by the at least one prediction model for predicting the predicted result of the intradialytic hypotension according to the future data and corresponding actual data, comprising:
adjusting a number of at least one positive sample and at least one negative sample in the training data according to a number ratio, wherein the number ratio is a ratio of an expected number of the at least one positive sample and the at least one negative sample, the at least one positive sample is a sample related to the intradialytic hypotension occurring in the actual data, and the at least one negative sample is a sample related to the intradialytic hypotension not occurring in the actual data; and
training a new prediction model according to resampled training data.

2. The intradialytic analysis method according to claim 1, wherein the step of determining the final future data according to the future data predicted by the prediction models comprises:
determining a statistical indicator of the future data predicted by the prediction models based on ensemble learning, wherein machine learning algorithms used by the prediction models are different.

3. The intradialytic analysis method according to claim 1, wherein the variance relation comprises at least one of an ultrafiltration rate change, a conductivity change, a dialysate temperature change, a blood flow change, a dehydration rate difference, a venous pressure difference, a dialysis time difference, a dialysate flow difference, a systolic blood pressure difference, and a pulse difference, the variance relation is changes in data between t and t–1 or between t–1 and t–2, t is a current time point, and t–1 and t–2 are previous time points.

4. The intradialytic analysis method according to claim 1, wherein the previous data comprises at least one of blood pressure information before a current dialysis operation and statistical information of a previous dialysis operation.

5. The intradialytic analysis method according to claim 1, further comprising:
predicting the future data again through the new prediction model.

6. The intradialytic analysis method according to claim 1 wherein
at least one of the at least one positive sample and the at least one negative sample is copied; and/or at least one of the at least one positive sample and the at least one negative sample is deleted.

7. The intradialytic analysis method according to claim 1, further comprising:

emitting a warning notification according to the blood pressure information or the predicted result of the intradialytic hypotension at the future time point.

8. The intradialytic analysis method according to claim 1, further comprising:

converting the operating parameter of the dialysis machine and/or the data related to the tester into the at least one input feature, wherein the at least one input feature conforms to an input format of the at least one prediction model.

9. An analysis apparatus for dialysis, comprising:

a storage, configured to store a code; and a processor, coupled to the storage and configured to load and execute the code to:

obtain at least one input feature, wherein the at least one input feature comprises variance relation between current data and previous data of an operating parameter related to a dialysis machine and data related to a tester; and predict future data according to the at least one input feature through at least one prediction model, wherein the future data comprises blood pressure information and a predicted result of intradialytic hypotension at a future time point, the at least one prediction model comprises a plurality of first classification models and a plurality of second classification models, and the processor is further configured to:

determine final future data according to the future data predicted by the first and second prediction models, wherein the final future data comprises the blood pressure information and the predicted result of the intradialytic hypotension at the future time point, and the blood pressure information indicates systolic blood pressure;

determine the blood pressure information in the future data predicted by the first classification models;

determine the predicted result of the intradialytic hypotension in the future data predicted by the second classification models according to the at least one input feature and the blood pressure information, resample a plurality of training data used by the at least one prediction model for predicting the predicted result of the intradialytic hypotension according to the future data and corresponding actual data, comprising:

adjust a number of at least one positive sample and at least one negative sample in the training data according to a number ratio, wherein the number ratio is a ratio of an expected number of the at least one positive sample and the at least one negative sample, the at least one positive sample is a sample related to the intradialytic hypotension occurring in the actual data, and the at least one negative sample is a sample related to the intradialytic hypotension not occurring in the actual data; and train a new prediction model according to resampled training data.

10. The analysis apparatus for dialysis according to claim 9, wherein the processor is further configured to:

determine a statistical indicator of the future data predicted by the prediction models based on ensemble learning, wherein machine learning algorithms used by the prediction models are different.

11. The analysis apparatus for dialysis according to claim 9, wherein the variance relation comprises at least one of an ultrafiltration rate change, a conductivity change, a dialysate temperature change, a blood flow change, a dehydration rate difference, a venous pressure difference, a dialysis time difference, a dialysate flow difference, a systolic blood pressure difference, and a pulse difference, the variance relation is changes in data between t and t−1 or between t−1 and t−2, t is a current time point, and t−1 and t−2 are previous time points.

12. The analysis apparatus for dialysis according to claim 9, wherein the previous data comprises at least one of blood pressure information before a current dialysis operation and statistical information of a previous dialysis operation.

13. The analysis apparatus for dialysis according to claim 9, wherein the processor is further configured to:

predict the future data again through the new prediction model.

14. The analysis apparatus for dialysis according to claim 9, wherein at least one of the at least one positive sample and the at least one negative sample is copied; and/or at least one of the at least one positive sample and the at least one negative sample is deleted.

15. The analysis apparatus for dialysis according to claim 9, further comprising:

a prompt apparatus, coupled to the processor, wherein the processor is further configured to:

emit a warning notification according to the predicted result of the intradialytic hypotension through the prompt apparatus.

16. The analysis apparatus for dialysis according to claim 9, wherein the processor is further configured to:

convert the operating parameter of the dialysis machine and/or the data related to the tester into the at least one input feature, wherein the at least one input feature conforms to an input format of the at least one prediction model.

* * * * *